(12) United States Patent
Cao et al.

(10) Patent No.: US 11,417,791 B2
(45) Date of Patent: Aug. 16, 2022

(54) RADIATION DETECTOR WITH QUANTUM DOT SCINTILLATOR

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 113 days.

(21) Appl. No.: 16/919,643

(22) Filed: Jul. 2, 2020

(65) Prior Publication Data
US 2020/0335653 A1    Oct. 22, 2020

Related U.S. Application Data

(63) Continuation of application No. PCT/CN2018/074150, filed on Jan. 25, 2018.

(51) Int. Cl.
| | | |
|---|---|---|
| *G01T 1/20* | (2006.01) | |
| *G01N 23/046* | (2018.01) | |
| *G01V 5/00* | (2006.01) | |
| *H01J 37/244* | (2006.01) | |
| *H01L 31/0352* | (2006.01) | |
| *H01L 31/118* | (2006.01) | |
| *A61B 6/03* | (2006.01) | |
| *A61B 6/14* | (2006.01) | |

(Continued)

(52) U.S. Cl.
CPC ............. *H01L 31/118* (2013.01); *A61B 6/032* (2013.01); *A61B 6/14* (2013.01); *A61B 6/50* (2013.01); *G01N 23/046* (2013.01); *G01T 1/20184* (2020.05); *G01V 5/0016* (2013.01); *H01J 37/244* (2013.01); *H01L 31/035218* (2013.01); *B82Y 20/00* (2013.01)

(58) Field of Classification Search
CPC ........... H01L 31/118; H01L 31/035218; A61B 6/032; A61B 6/14; A61B 6/50; G01N 23/046; G01T 1/20184; G01T 1/2018; G01V 5/0016; H01J 37/244; B82Y 20/00
See application file for complete search history.

(56) References Cited

U.S. PATENT DOCUMENTS

2007/0085010 A1 *  4/2007  Letant ................. G01T 1/16
                                              250/361 R
2010/0246919 A1    9/2010  Wainer
(Continued)

FOREIGN PATENT DOCUMENTS

| CN | 106206636 A | 12/2016 |
|---|---|---|
| CN | 107356954 A | 11/2017 |

(Continued)

OTHER PUBLICATIONS

PCT/CN2018/074150 ISA210 ISR dated Oct. 25, 2018.

*Primary Examiner* — Courtney D Thomas
(74) *Attorney, Agent, or Firm* — IPro, PLLC; Qian Gu

(57) ABSTRACT

Disclosed herein is a radiation detector comprising: a layer of quantum dots configured to emit a pulse of visible light upon absorbing a radiation particle; an electronic system configured to detect the radiation particle by detecting the pulse of visible light.

22 Claims, 14 Drawing Sheets

(51) Int. Cl.
*A61B 6/00* (2006.01)
*B82Y 20/00* (2011.01)

(56) References Cited

U.S. PATENT DOCUMENTS

| | | | |
|---|---|---|---|
| 2012/0199747 A1* | 8/2012 | Letant | ........................ G01T 3/06 250/362 |
| 2018/0017685 A1 | 1/2018 | Cao | |
| 2018/0017686 A1 | 1/2018 | Cao et al. | |

FOREIGN PATENT DOCUMENTS

| | | |
|---|---|---|
| DE | 102006017291 B4 | 5/2017 |
| WO | 2017025888 A1 | 2/2017 |

\* cited by examiner

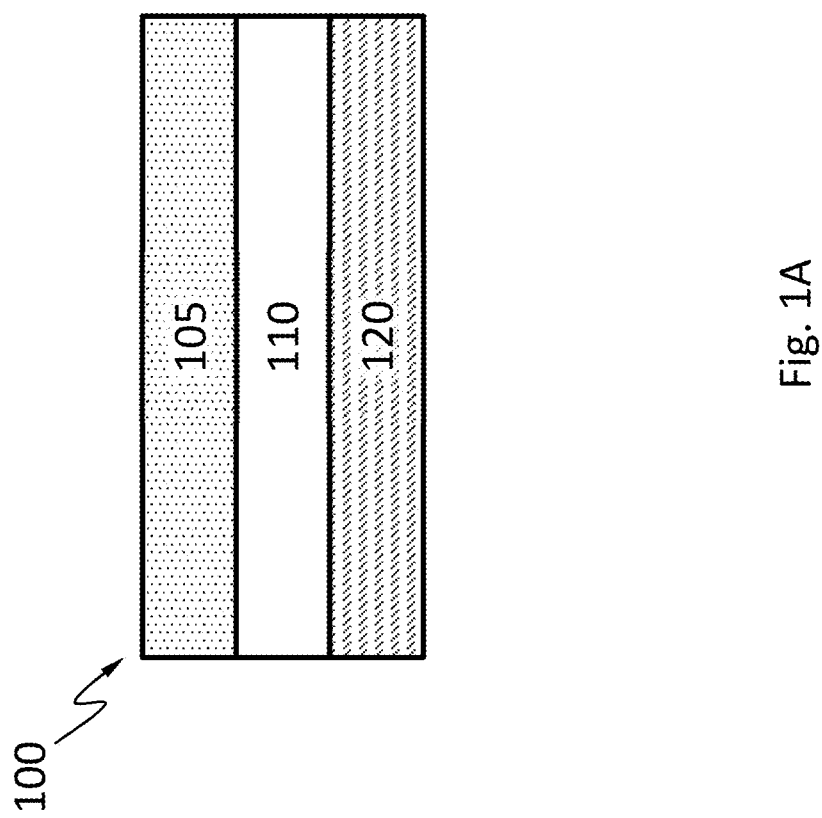

RADIATION DETECTOR WITH QUANTUM DOT SCINTILLATOR

TECHNICAL FIELD

The disclosure herein relates to a radiation detector, particularly relates to radiation detector comprising quantum dot scintillator.

BACKGROUND

A radiation detector is a device that measures a property of a radiation. Examples of the property may include a spatial distribution of the intensity, phase, and polarization of the radiation. The radiation may be one that has interacted with a subject. For example, the radiation measured by the radiation detector may be a radiation that has penetrated or reflected from the subject. The radiation may be an electromagnetic radiation such as infrared light, visible light, ultraviolet light, X-ray or γ-ray. The radiation may be of other types such as α-rays and β-rays.

One type of radiation detectors uses a scintillator. Scintillators operate somewhat similarly to image intensifiers in that scintillators (e.g., sodium iodide) absorb the radiation (e.g., X-ray) incident on a detector and emit a different radiation (e.g., visible light), which can then be detected by a suitable sensor. Due to material characteristics, traditional scintillators may have low light conversion efficiency and slower conversion speed, which limits applications in radiation and X-ray imaging that require large imaging area and fast radiation response.

SUMMARY

Disclosed herein is a radiation detector comprising: a layer of quantum dots configured to emit a pulse of visible light upon absorbing a radiation particle; an electronic system configured to detect the radiation particle by detecting the pulse of visible light.

According to an embodiment, the quantum dots are selected from a group consisting of lead iodide (PbI) quantum dots, CdZnTe (CZT) quantum dots, cesium iodide (CsI) quantum dots, bismuth germanate (BGO) quantum dots, cadmium tungstate $CdWO_4$ quantum dots, calcium tungstate ($CaWO_4$) quantum dots, gadolinium oxysulfide ($Gd_2O_2S$) quantum dots, cerium doped lanthanum bromide ($LaBr_3$ (Ce)) quantum dots, cerium doped lanthanum chloride ($LaCl_3$(Ce)) quantum dots, lead tungstate ($PbWO_4$) quantum dots lutetium oxyorthosilicate ($Lu_2SiO_5$ or LSO) quantum dots, $Lu_{1.8}Y_{0.2}SiO_5(Ce)$ (LYSO) quantum dots, thallium doped sodium iodide (NaI(Tl)) quantum dots, yttrium aluminum garnet (YAG(Ce)) quantum dots, zinc sulfide (ZnS (Ag)) quantum dots, zinc tungstate (ZnWO4) quantum dots, and combinations thereof.

According to an embodiment, the radiation detector further comprises a visible light absorption layer configured to generate an electric signal upon absorbing the pulse of visible light; wherein the electronic system is configured to detect the pulse of visible light based on the electric signal.

According to an embodiment, the electronic system is configured to count a number of radiation particles absorbed by the layer of quantum dots by counting a number of pulses of visible light.

According to an embodiment, the electronic system comprises a plurality of pixels, each of which is configured to detect the pulse of visible light.

According to an embodiment, the electronic system comprises a counter configured to count a number of pulses of visible light received by a pixel of the plurality pixels.

According to an embodiment, the pixels are configured to operate in parallel.

According to an embodiment, the ADC is a successive-approximation-register (SAR) ADC.

According to an embodiment, the radiation particle is an X-ray photon.

According to an embodiment, the visible light absorption layer comprises an electric contact; wherein the electronic system comprises: a first voltage comparator configured to compare a voltage of the electric contact to a first threshold; a second voltage comparator configured to compare the voltage to a second threshold; a counter configured to register a number of pulses of visible light received by the visible light absorption layer; a controller; wherein the controller is configured to start a time delay from a time at which the first voltage comparator determines that an absolute value of the voltage equals or exceeds an absolute value of the first threshold; wherein the controller is configured to activate the second voltage comparator during the time delay; wherein the controller is configured to cause the number registered by the counter to increase by one, upon determination by the second voltage comparator that an absolute value of the voltage equals or exceeds an absolute value of the second threshold.

According to an embodiment, the radiation detector further comprises a capacitor module electrically connected to the electric contact, wherein the capacitor module is configured to collect charge carriers from the electric contact.

According to an embodiment, the controller is configured to activate the second voltage comparator at a beginning or expiration of the time delay.

According to an embodiment, the controller is configured to connect the electric contact to an electrical ground.

According to an embodiment, the rate of change of the voltage is substantially zero at expiration of the time delay.

According to an embodiment, the visible light absorption layer comprises a diode.

According to an embodiment, the visible light absorption layer comprises silicon or germanium.

Disclosed herein is a system comprising the radiation detector described above and a radiation source, wherein the system is configured to perform radiation radiography on human chest or abdomen.

Disclosed herein is a system comprises the radiation detector described above and a radiation source, wherein the system is configured to perform radiation radiography on human mouth and teeth.

Disclosed herein is a cargo scanning or non-intrusive inspection (NII) system, comprising the radiation detector described above and a radiation source, wherein the cargo scanning or non-intrusive inspection (NII) system is configured to form an image using backscattered radiation.

Disclosed herein is a cargo scanning or non-intrusive inspection (NII) system, comprising the radiation detector described above and a radiation source, wherein the cargo scanning or non-intrusive inspection (NII) system is configured to form an image using radiation transmitted through an object inspected.

Disclosed herein is a full-body scanner system comprising the radiation detector described above and a radiation source.

Disclosed herein is a radiation computed tomography (X-ray CT) system comprising the radiation detector described above and a radiation source.

Disclosed herein is an electron microscope comprising the apparatus described above, an electron source and an electronic optical system.

BRIEF DESCRIPTION OF FIGURES

FIG. 1A schematically shows a cross-sectional view of a radiation detector, according to an embodiment.

DETAILED DESCRIPTION

Figure 1B:
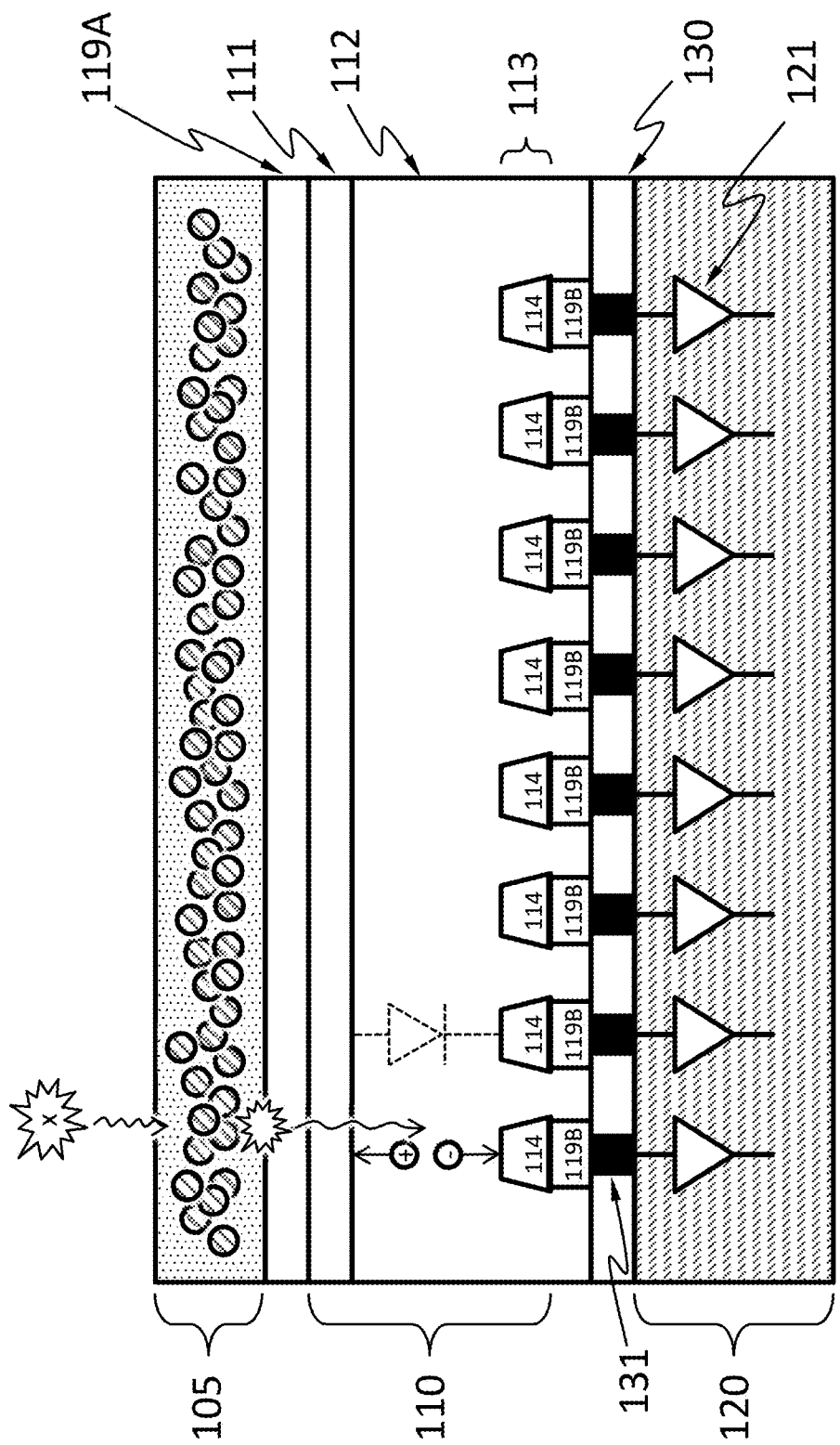
FIG. 1B schematically shows a detailed cross-sectional view of the radiation detector.

FIG. 1A schematically shows a cross-sectional view of the radiation detector 100, according to an embodiment. The radiation detector 100 may include a layer of quantum dots 105, a visible light absorption layer 110 and an electronics layer 120 (e.g., an ASIC) for processing or analyzing electrical signals generated in the visible light absorption layer 110. The layer of quantum dot 105 may comprise a plurality of quantum dots such as lead iodide (PbI) quantum dots, CdZnTe (CZT) quantum dots, cesium iodide (CsI) quantum dots, bismuth germanate (BGO) quantum dots, cadmium tungstate $CdWO_4$ quantum dots, calcium tungstate ($CaWO_4$) quantum dots, gadolinium oxysulfide ($Gd_2O_2S$) quantum dots, cerium doped lanthanum bromide ($LaBr_3$(Ce)) quantum dots, cerium doped lanthanum chloride ($LaCl_3$(Ce)) quantum dots, lead tungstate ($PbWO_4$) quantum dots lutetium oxyorthosilicate ($Lu_2SiO_5$ or LSO) quantum dots, $Lu_{1.8}Y_{0.2}SiO_5$(Ce) (LYSO) quantum dots, thallium doped sodium iodide (NaI(TI)) quantum dots, yttrium aluminum garnet (YAG(Ce)) quantum dots, zinc sulfide (ZnS (Ag)) quantum dots, and zinc tungstate (ZnWO4) quantum dots. The layer of quantum dots 105 may emit a pulse of visible light upon absorbing a radiation particle incident thereon. The visible light absorption layer 110 may include a semiconductor material such as silicon, germanium, or a combination thereof. The semiconductor material may have a high mass attenuation coefficient for the visible light emitted from the layer of quantum dots 105.

As shown in a detailed cross-sectional view of the radiation detector 100 in FIG. 1B, according to an embodiment, the layer of quantum dot 105 may include many quantum dots dispersed in a matrix. The layer of quantum dot 105 may emit a pulse of visible light when the layer of quantum dots 105 absorbs a radiation particle incident thereon. One example of the mechanism for the emission of the pulse of visible light is fluorescence. The radiation particle may be an X-ray photon. The pulse of visible light emitted from the layer of quantum dots 105 may be directed toward the visible light absorption layer 110. The visible light absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete portions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 1B, each of the discrete regions 114 of the second doped region 113 forms a diode with the first doped region 111 and the optional intrinsic region 112. Namely, in the example in FIG. 1B, the visible light absorption layer 110 has a plurality of diodes having the first doped region 111 as a shared electrode. The first doped region 111 may also have discrete portions.

When the pulse of visible light from the layer of quantum dots 105 hits the visible light absorption layer 110 including diodes, the visible light may be absorbed and generate one or more charge carriers by a number of mechanisms. A pulse of visible light may generate 1 to 100000 charge carriers. The charge carriers may drift to the electrodes of one of the diodes under an electric field. The field may be an external electric field. The electrical contact 119B may include discrete portions each of which is in electrical contact with the discrete regions 114. In an embodiment, the charge carriers may drift in directions such that the charge carriers generated by a single pulse of visible light are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). A pixel 150 associated with a discrete region 114 may be an area around the discrete region 114 in which substantially all (more than 98%, more than 99.5%, more than 99.9%, or more than 99.99% of) charge carriers generated by a pulse of visible light therein flow to the discrete region 114. Namely, less than 2%, less than 1%, less than 0.1%, or less than 0.01% of these charge carriers flow beyond the pixel.

Figure 1C:
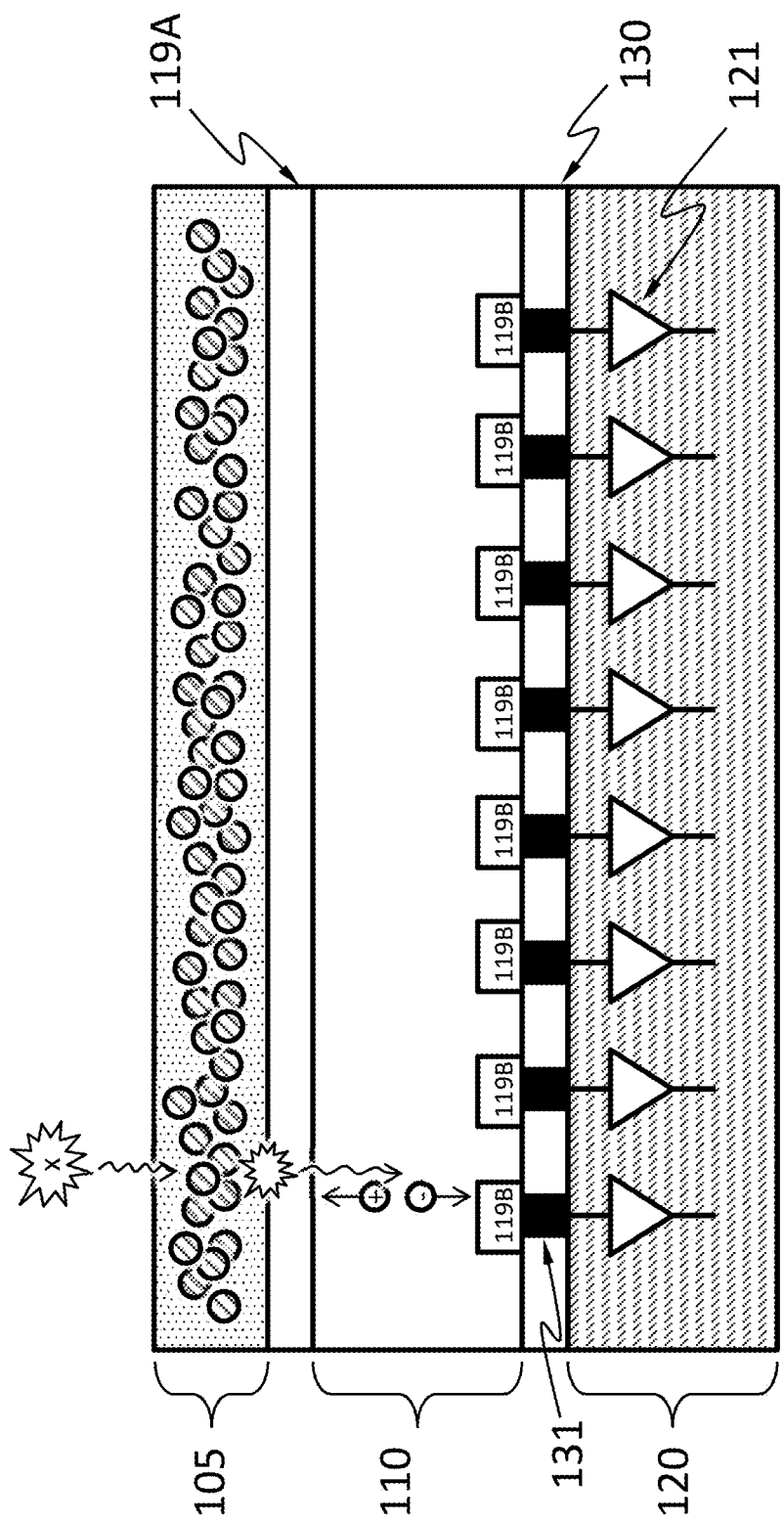
FIG. 1C schematically shows an alternative detailed cross-sectional view of the radiation detector.

As shown in an alternative detailed cross-sectional view of the radiation detector 100 in FIG. 1C, according to an embodiment, the visible light absorption layer 110 may include a resistor of a semiconductor material such as, silicon, germanium, or a combination thereof, but does not include a diode. The semiconductor may have a high mass attenuation coefficient for the visible light emitted from the layer of quantum dots 105.

When the pulse of visible light from the layer of quantum dots 105 hits the visible light absorption layer 110 including a resistor but not diodes, it may be absorbed and generate one or more charge carriers by a number of mechanisms. A pulse of visible light may generate 1 to 100000 charge carriers. The charge carriers may drift to the electrical contacts 119A and 119B under an electric field. The field may be an external electric field. The electrical contact 119B includes discrete portions. In an embodiment, the charge carriers may drift in directions such that the charge carriers generated by a single pulse of visible light are not substantially shared by two different discrete portions of the electrical contact 119B ("not substantially shared" here means less than 2%, less than 0.5%, less than 0.1%, or less than 0.01% of these charge carriers flow to a different one of the discrete portions than the rest of the charge carriers). A pixel 150 associated with a discrete portion of the electrical contact 119B may be an area around the discrete portion in which substantially all (more than 98%, more than 99.5%, more than 99.9% or more than 99.99% of) charge carriers generated by a pulse of visible light incident therein flow to the discrete portion of the electrical contact 119B. Namely, less than 2%, less than 0.5%, less than 0.1%, or less than 0.01% of these charge carriers flow beyond the pixel associated with the one discrete portion of the electrical contact 119B.

The electronics layer 120 may include an electronic system 121 suitable for processing or interpreting electric signals generated by the pulse of visible light incident on the visible light absorption layer 110. The electronic system 121 is configured to count a number of radiation particles absorbed by the layer of quantum dots 105 by counting a number of pulses of visible light emitted from the layer of quantum dots 105, according to an embodiment. The electronic system 121 may include an analog circuitry such as a filter network, amplifiers, integrators, and comparators, or a digital circuitry such as a microprocessor, and memory. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the electrical contacts 119B by vias 131. Space among the vias may be filled with a filler material 130, which may increase the mechanical stability of the connection of the electronics layer 120 to the visible light absorption layer 110. Other bonding techniques are possible to connect the electronic system 121 to the pixels without using vias.

Figure 2:
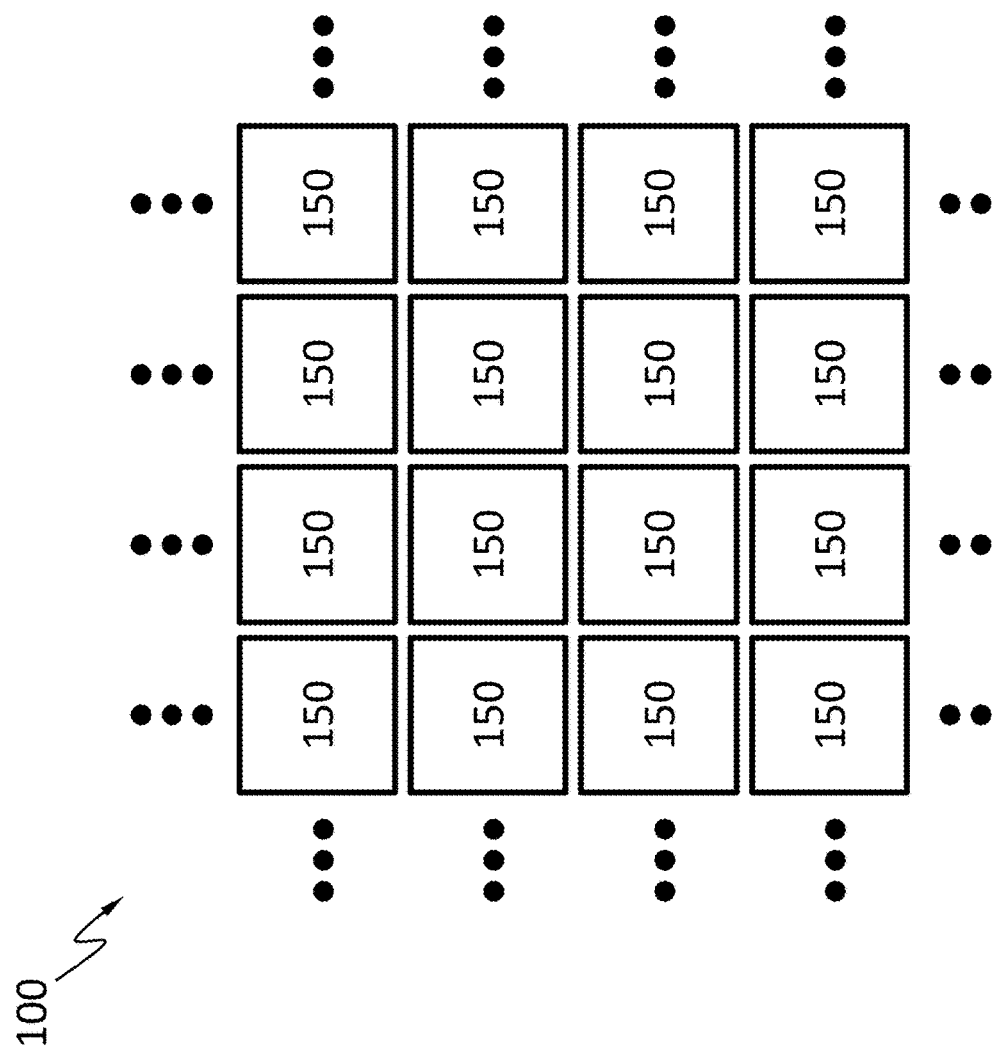
FIG. 2 shows an exemplary top view of a portion of the detector in FIG. 1A, according to an embodiment.

FIG. 2 schematically shows that pixels 150 in the radiation detector 100 may be arranged in an array, according to an embodiment. The array may be a rectangular array, a honeycomb array, a hexagonal array or any other suitable array. A characteristic (e.g., the intensity) of the pulse of visible light incident in each pixel 150 may be measured. For example, numbers of pulses of visible light incident on each pixel 150 within a period of time may be counted. The numbers of pulses of visible light incident on all the pixels 150 within the same period of time may be counted. An analog-to-digital converter (ADC) may be configured to digitize an analog signal representing the characteristic of the pulse of visible light incident on each pixel 150. The pixels 150 may be configured to operate in parallel. For example, when one pixel 150 has a pulse of visible light incident thereon, another pixel 150 may or may not have a pulse of visible light incident thereon. The pixels 150 may not have to be individually addressable. In an example, the pixels 150 include photodiodes configured to detect pulses of visible light from the layer of quantum dots 105. The photodiodes may front-illuminated, side-illuminated or back-illuminated.

The radiation detector 100 may have at least 100, 2500, 10000, or more pixels 150.

Figure 3A:
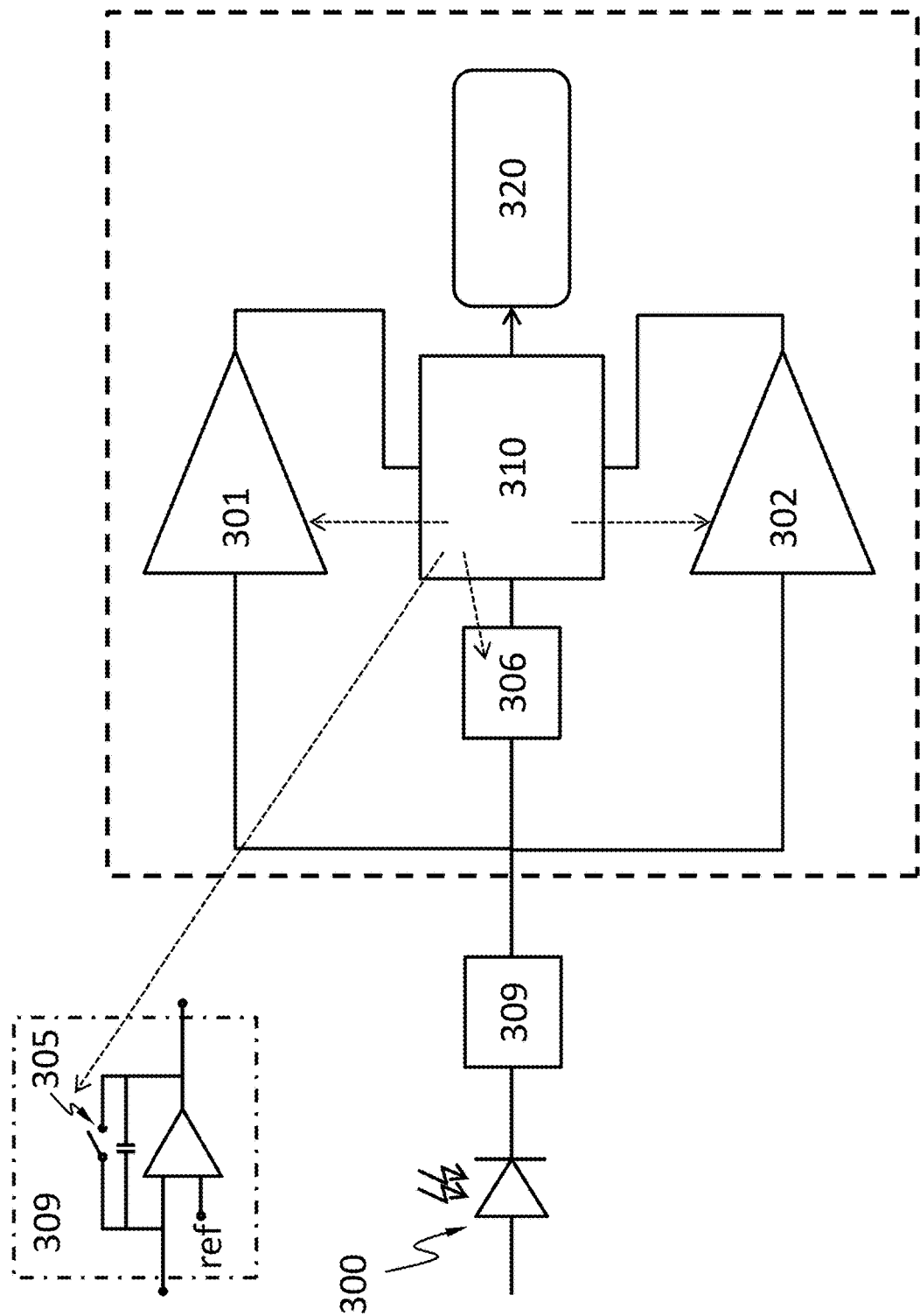
FIG. 3A and FIG. 3B each schematically show a component diagram of the electronic system of the detector, according to an embodiment.
Figure 3B:
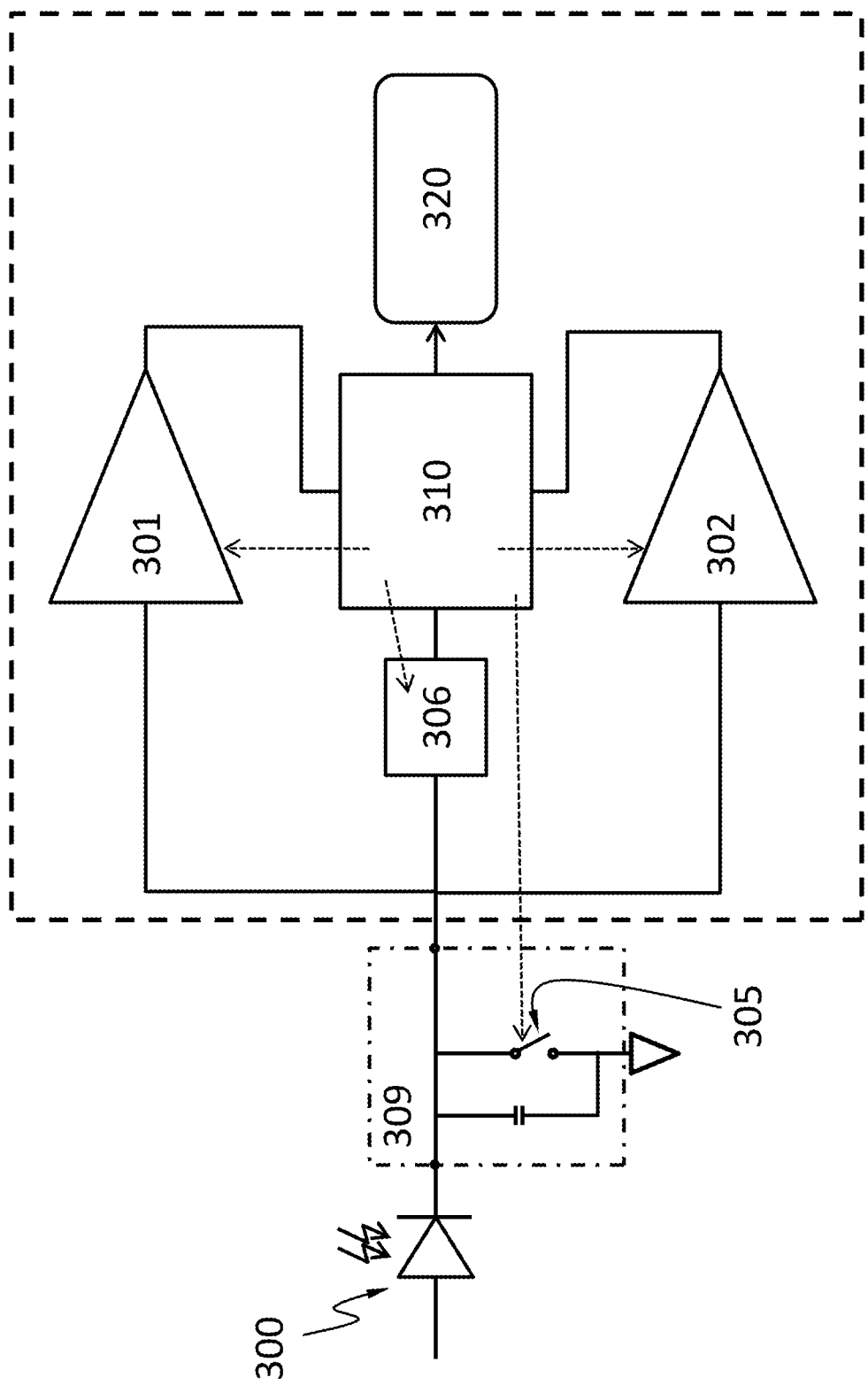

FIG. 3A and FIG. 3B each show a component diagram of the electronic system 121, according to an embodiment. The electronic system 121 may include a first voltage comparator 301, a second voltage comparator 302, a counter 320, a switch 305, a voltmeter 306 and a controller 310.

The first voltage comparator 301 is configured to compare the voltage of the electrical contact 119B to a first threshold. The first voltage comparator 301 may be configured to monitor the voltage directly, or calculate the voltage by integrating an electric current flowing through the electrical contact over a period of time. The first voltage comparator 301 may be controllably activated or deactivated by the controller 310. The first voltage comparator 301 may be a continuous comparator. Namely, the first voltage comparator 301 may be configured to be activated continuously, and monitor the voltage continuously. The first voltage comparator 301 configured as a continuous comparator reduces the chance of the system 121 missing signals generated by a pulse of visible light. The first voltage comparator 301 may be a clocked comparator, which has the benefit of lower power consumption. The first threshold may be 5-10%, 10%-20%, 20-30%, 30-40% or 40-50% of the voltage a single pulse of visible light may generate on the electrical contact. The maximum voltage may depend on the energy of the pulse of visible light, the material of the visible light absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly, or calculate the voltage by integrating an electric current flowing through the diode or the electrical contact over a period of time. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, \text{ if } x \geq 0 \\ -x, \text{ if } x \leq 0 \end{cases}.$$

The second threshold may be 200%-300% of the first threshold. The second threshold may be at least 50% of the maximum voltage one pulse of visible light may generate on the electrical contact 119B. For example, the second threshold may be 100 mV, 150 mV, 200 mV, 250 mV or 300 mV. The second voltage comparator 302 and the first voltage comparator 301 may be the same component. Namely, the system 121 may have one voltage comparator that can compare a voltage with two different thresholds at different times.

The first voltage comparator 301 or the second voltage comparator 302 may include one or more op-amps or any other suitable circuitry.

The counter 320 is configured to register a number of pulses of visible light reaching a pixel. The counter 320 may be a software component (e.g., a number stored in a computer memory) or a hardware component (e.g., a 4017 IC and a 7490 IC).

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 310 may be configured to keep deactivated the counter 320 and any other circuits the operation of the first voltage comparator 301 does not require, before the time at which the first voltage comparator 301 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "to activate a component" means causing the component to enter an operational state (e.g., by sending a signal such as a voltage pulse or a logic level, by providing power, etc.). The term "to deactivate a component" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause the number registered by the counter 320 to increase by one, if, during the time delay, the second voltage comparator 302 determines that the absolute value of the voltage equals or exceeds the absolute value of the second threshold.

The controller 310 may be configured to cause the voltmeter 306 to measure the voltage upon expiration of the time delay. The controller 310 may be configured to connect the electrical contact to an electrical ground, so as to reset the voltage and discharge any charge carriers accumulated on the electrical contact. In an embodiment, the electrical contact is connected to an electrical ground after the expiration of the time delay. In an embodiment, the electrical contact is connected to an electrical ground for a finite reset time period. The controller 310 may connect the electrical contact to the electrical ground by controlling the switch 305. The switch may be a transistor such as a field-effect transistor (FET).

In an embodiment, the system 121 has no analog filter network (e.g., a RC network). In an embodiment, the system 121 has no analog circuitry.

The voltmeter 306 may feed the voltage it measures to the controller 310 as an analog or digital signal.

Figure 4:
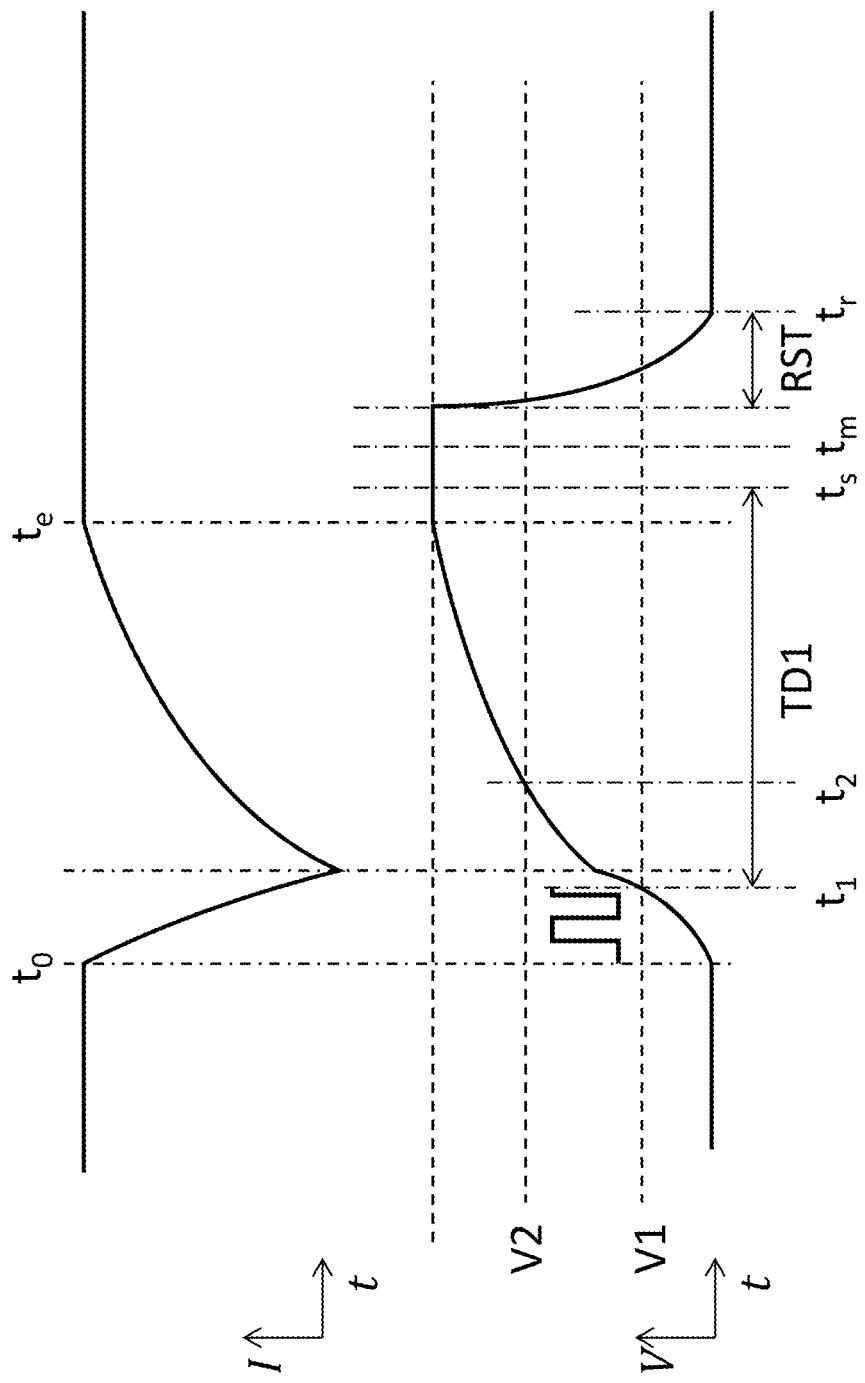
FIG. 4 schematically shows a temporal change of the electric current flowing through an electric contact (upper curve) caused by charge carriers generated by a pulse of visible light incident on a pixel associated with the electric contact, and a corresponding temporal change of the voltage of the electric contact (lower curve).

The system 121 may include a capacitor module 309 electrically connected to the electrode of the diode 300 or the electrical contact, wherein the capacitor module is configured to collect charge carriers from the electrical contact. The capacitor module can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electrode or the electrical contact accumulate on the capacitor over a period of time ("integration period") (e.g., as shown in FIG. 4, between $t_0$ to $t_1$). After the integration period has expired, the capacitor voltage is sampled and then reset by a reset switch. The capacitor module can include a capacitor directly connected to the electrode or the electrical contact.

FIG. 4 schematically shows a temporal change of the electric current flowing through the electric contact 119B (upper curve) caused by charge carriers generated by a pulse of visible light incident on the pixel 150 associated with the electric contact 119B, and a corresponding temporal change of the voltage of the electric contact 119B (lower curve). The voltage may be an integral of the electric current with respect to time. At time to, a radiation particle hits the detector, a pulse of visible light is emitted by the layer of quantum dots 105; the pulse of visible light is absorbed at a pixel 150 of the visible light absorption layer 110; charge carriers start being generated in the pixel 150; electric current starts to flow through the electrical contact 119B; and the absolute value of the voltage of the electrical contact 119B starts to increase. At time $t_1$, the first voltage comparator 301 determines that the absolute value of the voltage equals or exceeds the absolute value of the first threshold V1, and the controller 310 starts the time delay TD1 and the controller 310 may deactivate the first voltage comparator 301 at the beginning of TD1. If the controller 310 is deactivated before $t_1$, the controller 310 is activated at $t_1$. During TD1, the controller 310 activates the second voltage comparator 302. The term "during" a time delay as used here means the beginning and the expiration (i.e., the end) and any time in between. For example, the controller 310 may activate the second voltage comparator 302 at the expiration of TD1. If during TD1, the second voltage comparator 302 determines that the absolute value of the voltage equals or exceeds the absolute value of the second threshold at time $t_2$, the controller 310 waits for stabilization of the voltage to stabilize. The voltage stabilizes at time $t_e$, when all charge carriers generated by the pulse of visible light drift out of the visible light absorption layer 110. At time $t_s$, the time delay TD1 expires. At or after time $t_e$, the controller 310 may be configured to cause the voltmeter 306 to measure the voltage upon expiration of the time delay TD1. In an embodiment, the controller 310 causes the voltmeter 306 to measure the voltage after the rate of change of the voltage becomes substantially zero after the expiration of the time delay TD1. The voltage at this moment is proportional to the amount of charge carriers generated by a pulse of visible light, which relates to the energy of the radiation particle. The controller 310 may be configured to determine the energy of the radiation particle based on voltage the voltmeter 306 measures. One way to determine the energy is by binning the voltage. The counter 320 may have a sub-counter for each bin. When the controller 310 determines that the energy of the X-ray photon falls in a bin, the controller 310 may cause the number registered in the sub-counter for that bin to increase by one.

After TD1 expires, the controller 310 connects the electrode to an electric ground for a reset period RST to allow charge carriers accumulated on the electrode to flow to the ground and reset the voltage. After RST, the system 121 is ready to detect another incident X-ray photon.

Figure 5:
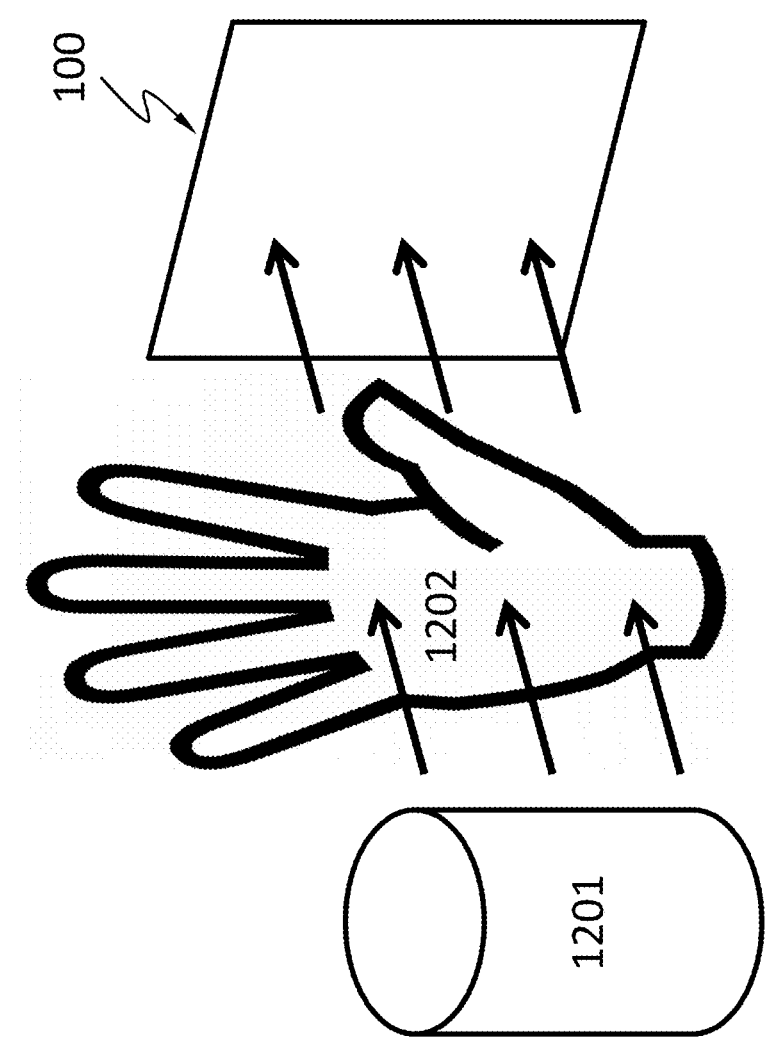
FIG. 5-FIG. 11 each schematically show a system comprising the radiation detector described herein.

FIG. 5 schematically shows a system comprising the radiation detector 100 described herein. The system may be used for medical imaging such as chest X-ray radiography, abdominal X-ray radiography, etc. The system comprises a pulsed radiation source 1201 that emits radiation. Radiation emitted from the pulsed radiation source 1201 penetrates an object 1202 (e.g., a human body part such as chest, limb, abdomen), is attenuated by different degrees by the internal structures of the object 1202 (e.g., bones, muscle, fat and organs, etc.), and is projected to the radiation detector 100. The radiation detector 100 forms an image by detecting the intensity distribution of the radiation.

Figure 6:
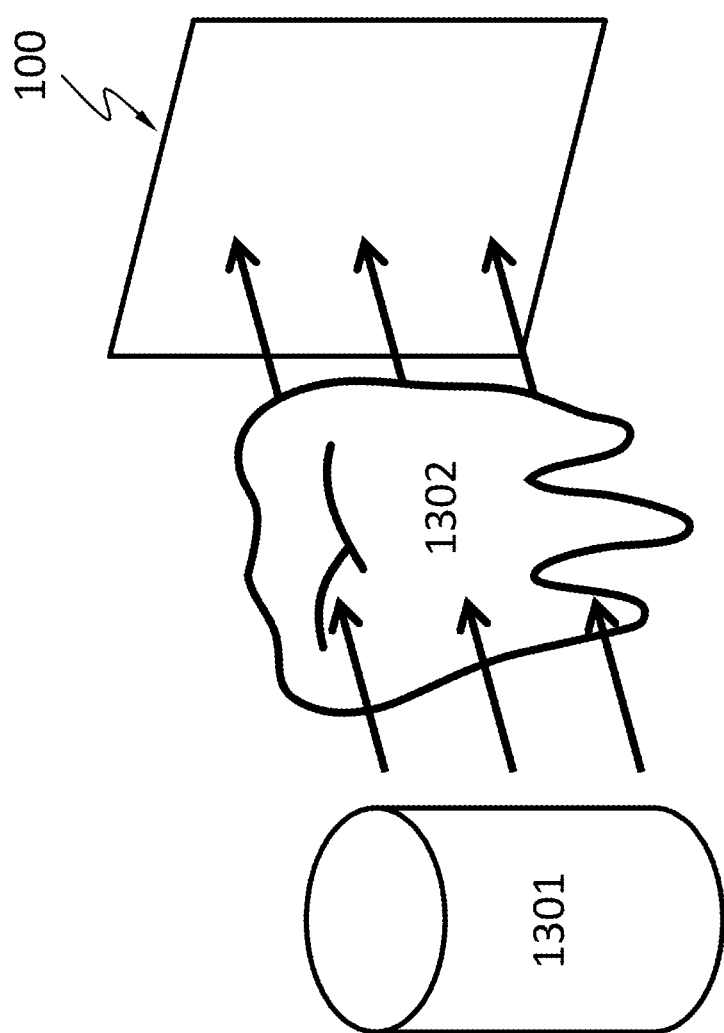

FIG. 6 schematically shows a system comprising the radiation detector 100 described herein. The system may be used for medical imaging such as dental X-ray radiography. The system comprises a pulsed radiation source 1301 that emits radiation. Radiation emitted from the pulsed radiation source 1301 penetrates an object 1302 that is part of a mammal (e.g., human) mouth. The object 1302 may include a maxilla bone, a palate bone, a tooth, the mandible, or the tongue. The radiation is attenuated by different degrees by the different structures of the object 1302 and is projected to the radiation detector 100. The radiation detector 100 forms an image by detecting the intensity distribution of the radiation. Teeth absorb radiation more than dental caries, infections, periodontal ligament. The dosage of radiation received by a dental patient is typically small (around 0.150 mSv for a full mouth series).

Figure 7:
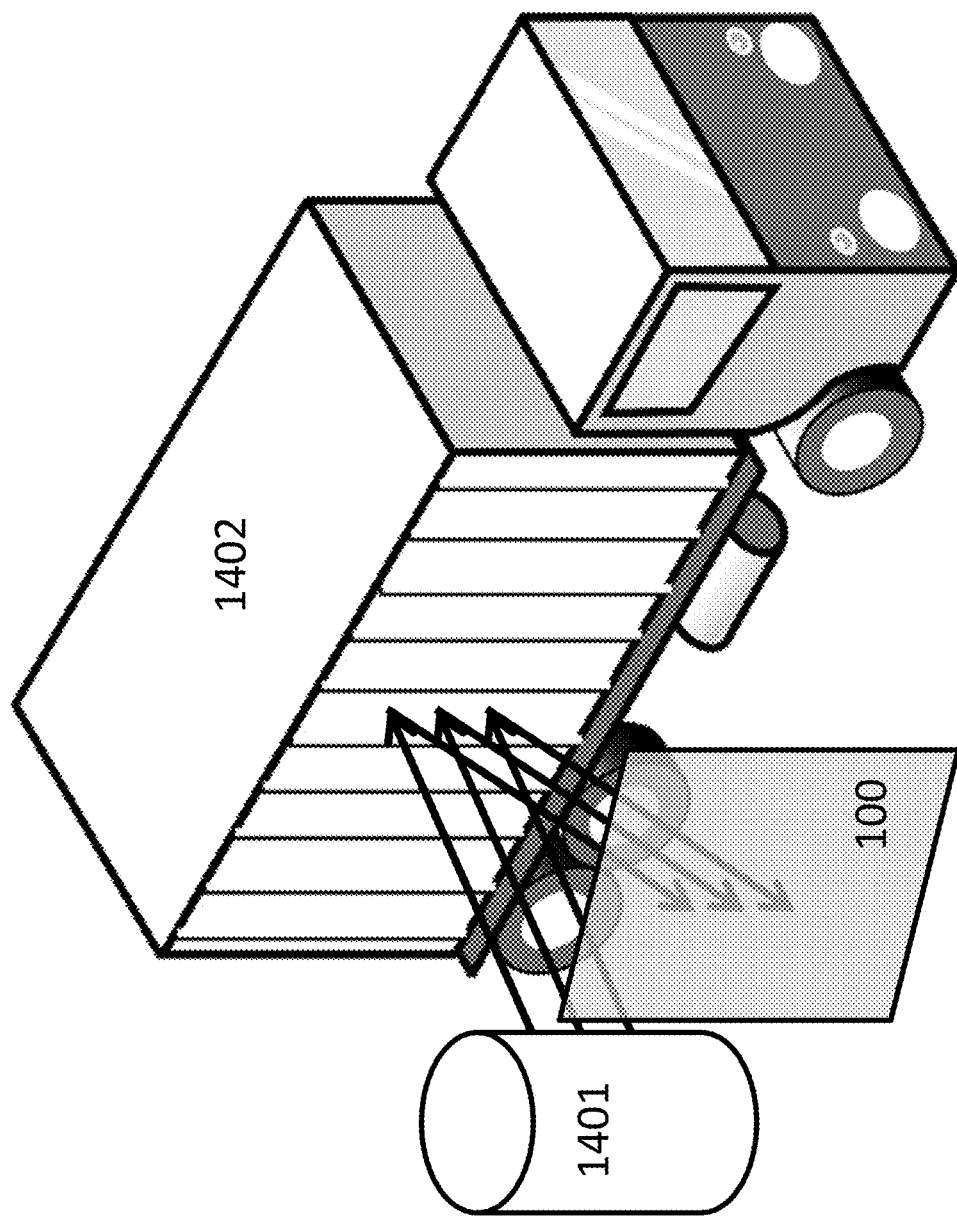

FIG. 7 schematically shows a cargo scanning or non-intrusive inspection (NII) system comprising the radiation detector 100 described herein. The system may be used for inspecting and identifying goods in transportation systems such as shipping containers, vehicles, ships, luggage, etc. The system comprises a pulsed radiation source 1401. Radiation emitted from the pulsed radiation source 1401 may backscatter from an object 1402 (e.g., shipping containers, vehicles, ships, etc.) and be projected to the radiation detector 100. Different internal structures of the object 1402 may backscatter the radiation differently. The radiation detector 100 forms an image by detecting the intensity distribution of the backscattered radiation and/or energies of the backscattered radiation.

Figure 8:
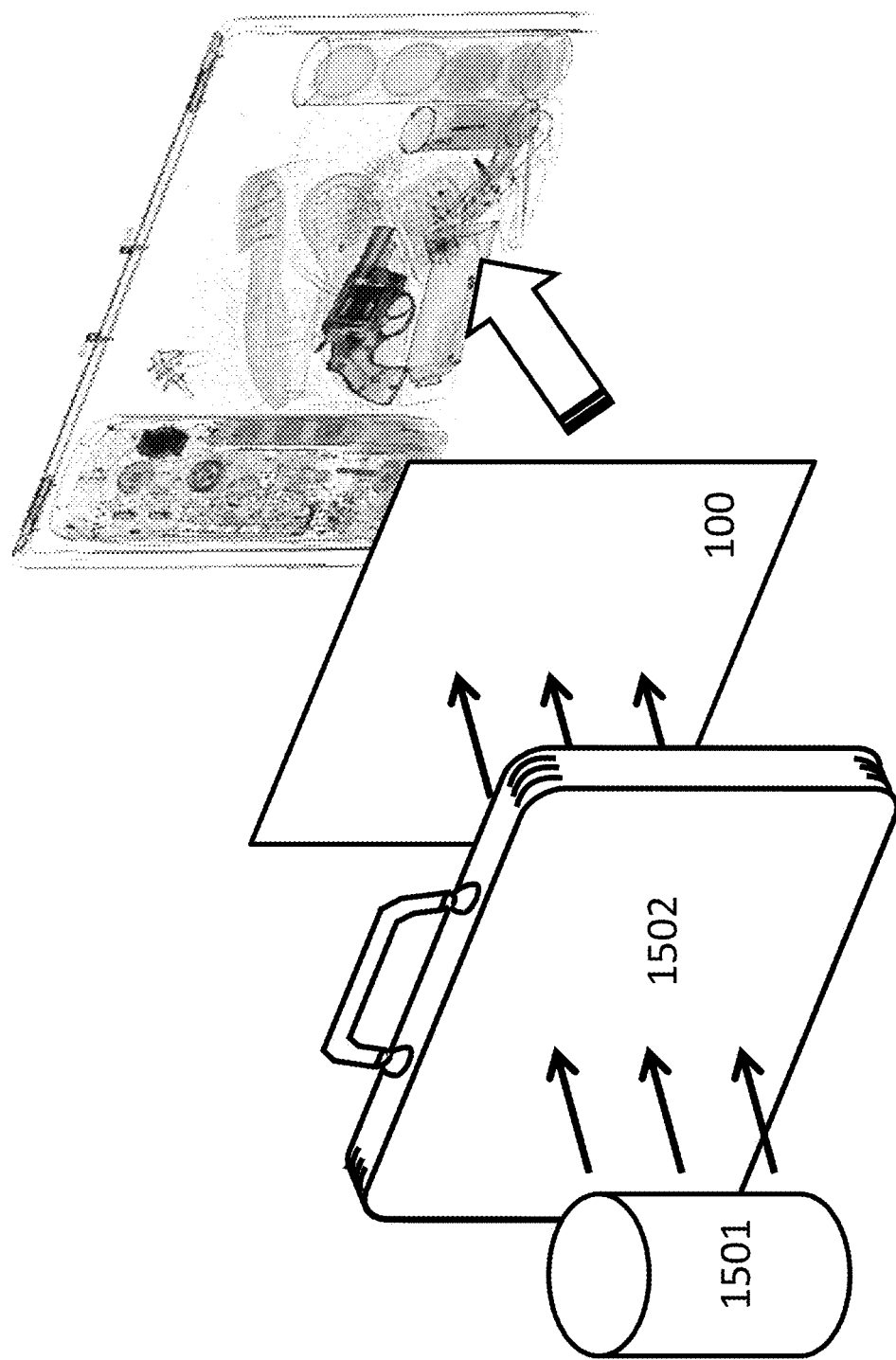

FIG. 8 schematically shows another cargo scanning or non-intrusive inspection (NII) system comprising the radiation detector 100 described herein. The system may be used for luggage screening at public transportation stations and airports. The system comprises a pulsed radiation source 1501 that emits radiation. Radiation emitted from the pulsed radiation source 1501 may penetrate a piece of luggage 1502, be differently attenuated by the contents of the luggage, and projected to the radiation detector 100. The radiation detector 100 forms an image by detecting the intensity distribution of the transmitted radiation. The system may reveal contents of luggage and identify items forbidden on public transportation, such as firearms, narcotics, edged weapons, flammables.

Figure 9:
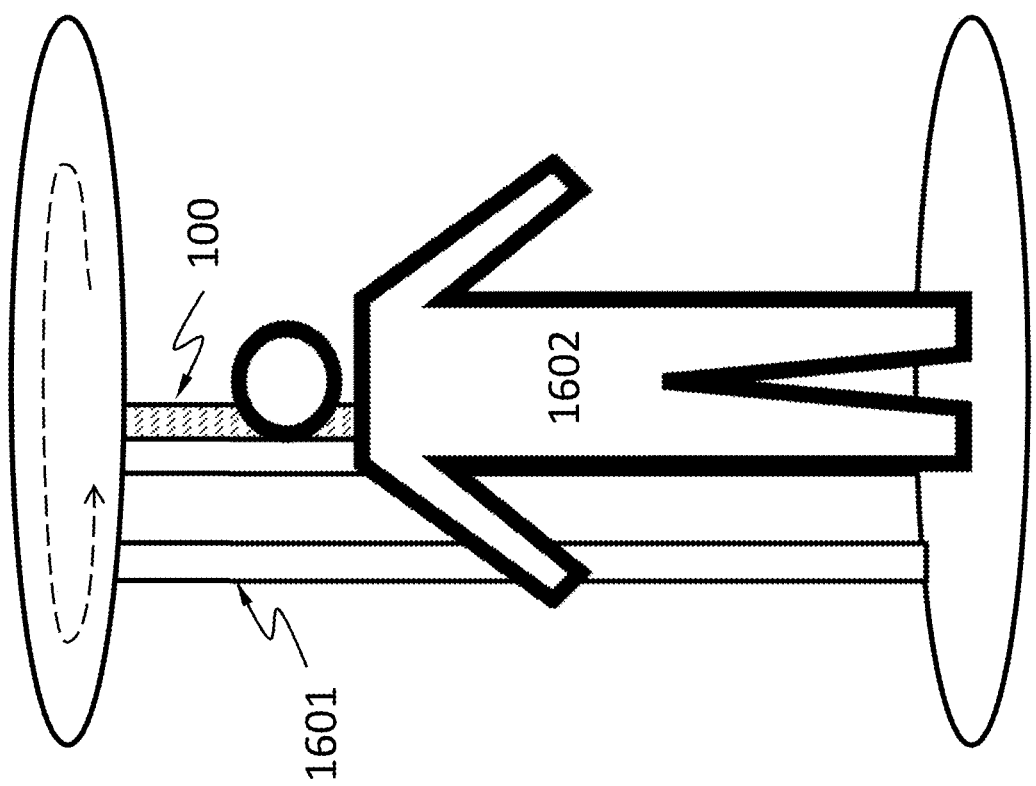

FIG. 9 schematically shows a full-body scanner system comprising the radiation detector 100 described herein. The full-body scanner system may detect objects on a person's body for security screening purposes, without physically removing clothes or making physical contact. The full-body scanner system may be able to detect non-metal objects. The full-body scanner system comprises a pulsed radiation source 1601. The radiation emitted from the pulsed radiation source 1601 may backscatter from a human 1602 being screened and objects thereon, and be projected to the radiation detector 100. The objects and the human body may backscatter the radiation differently. The radiation detector 100 forms an image by detecting the intensity distribution of the backscattered radiation. The radiation detector 100 and the pulsed radiation source 1601 may be configured to scan the human in a linear or rotational direction.

Figure 10:
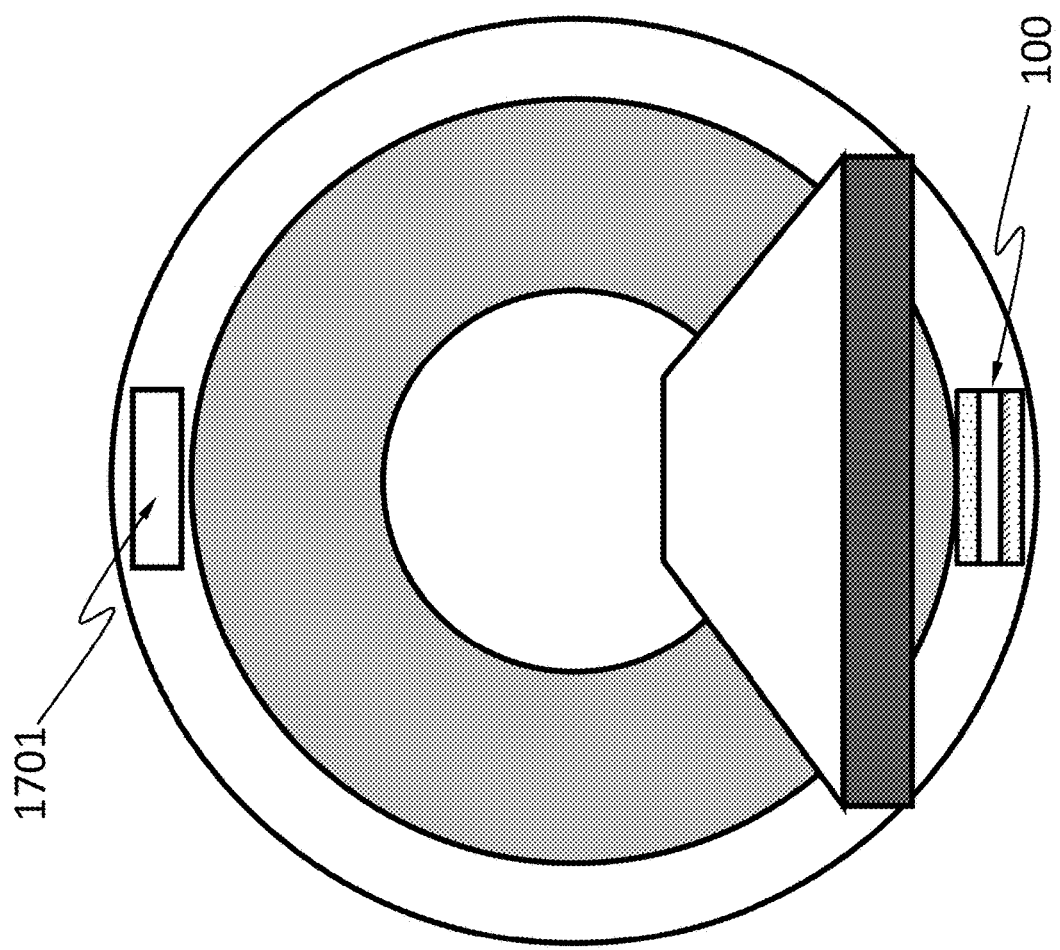

FIG. 10 schematically shows a radiation computed tomography (Radiation CT) system. The radiation CT system uses computer-processed radiations to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The radiation CT system comprises the radiation detector 100 described herein and a pulsed radiation source 1701 that emits radiation. The radiation detector 100 and the pulsed radiation source 1701 may be configured to rotate synchronously along one or more circular or spiral paths.

Figure 11:
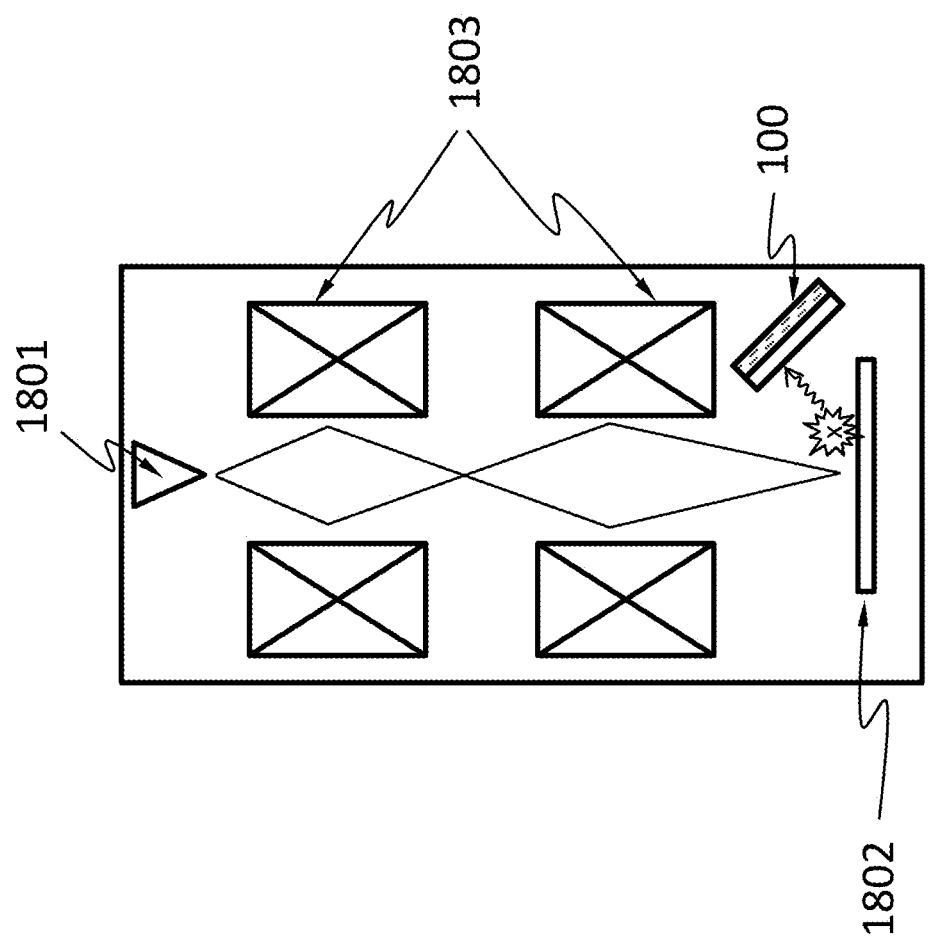

FIG. 11 schematically shows an electron microscope. The electron microscope comprises an electron source 1801 (also called an electron gun) that is configured to emit electrons. The electron source 1801 may have various emission mechanisms such as thermionic, photocathode, cold emission, or plasmas source. The emitted electrons pass through an electronic optical system 1803, which may be configured to shape, accelerate, or focus the electrons. The electrons then reach a sample 1802 and an image detector may form an image therefrom. The electron microscope may comprise the radiation detector 100 described herein, for performing energy-dispersive radiation spectroscopy (EDS). EDS is an analytical technique used for the elemental analysis or chemical characterization of a sample. When the electrons incident on a sample, they cause emission of characteristic radiations from the sample. The incident electrons may excite an electron in an inner shell of an atom in the sample, ejecting it from the shell while creating an electron hole where the electron was. An electron from an outer, higher-energy shell then fills the hole, and the difference in energy between the higher-energy shell and the lower energy shell may be released in the form of a radiation. The number and energy of the radiations emitted from the sample can be measured by the radiation detector 100.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A radiation detector, comprising:
a layer of quantum dots configured to emit a pulse of visible light upon absorbing a radiation particle;
an electronic system configured to detect the radiation particle by detecting the pulse of visible light; and
a visible light absorption layer configured to generate an electric signal upon absorbing the pulse of visible light;
wherein the electronic system is configured to detect the pulse of visible light based on the electric signal;
wherein the visible light absorption layer comprises an electric contact;
wherein the electronic system comprises:
a first voltage comparator configured to compare a voltage of the electric contact to a first threshold;
a second voltage comparator configured to compare the voltage to a second threshold;
a counter configured to register a number of pulses of visible light received by the visible light absorption layer;
a controller;
wherein the controller is configured to start a time delay from a time at which the first voltage comparator determines that an absolute value of the voltage equals or exceeds an absolute value of the first threshold;
wherein the controller is configured to activate the second voltage comparator during the time delay;

wherein the controller is configured to cause the number registered by the counter to increase by one, upon determination by the second voltage comparator that an absolute value of the voltage equals or exceeds an absolute value of the second threshold.

2. The radiation detector of claim 1, wherein the quantum dots are selected from a group consisting of lead iodide (PbI) quantum dots, CdZnTe (CZT) quantum dots, cesium iodide (CsI) quantum dots, bismuth germanate (BGO) quantum dots, cadmium tungstate $CdWO_4$ quantum dots, calcium tungstate ($CaWO_4$) quantum dots, gadolinium oxysulfide ($Gd_2O_2S$) quantum dots, cerium doped lanthanum bromide ($LaBr_3(Ce)$) quantum dots, cerium doped lanthanum chloride ($LaCl_3(Ce)$) quantum dots, lead tungstate ($PbWO_4$) quantum dots lutetium oxyorthosilicate ($Lu_2SiO_5$ or LSO) quantum dots, $Lu_{1.8}Y_{0.2}SiO_5(Ce)$ (LYSO) quantum dots, thallium doped sodium iodide (NaI(TI)) quantum dots, yttrium aluminum garnet (YAG(Ce)) quantum dots, zinc sulfide (ZnS(Ag)) quantum dots, zinc tungstate (ZnWO4) quantum dots, and combinations thereof.

3. The radiation detector of claim 1, wherein the electronic system is configured to count a number of radiation particles absorbed by the layer of quantum dots by counting a number of pulses of visible light.

4. The radiation detector of claim 1, wherein the electronic system comprises a plurality of pixels, each of which is configured to detect the pulse of visible light.

5. The radiation detector of claim 4, wherein the electronic system comprises a counter configured to count a number of pulses of visible light received by a pixel of the plurality of pixels.

6. The radiation detector of claim 4, wherein the pixels are configured to operate in parallel.

7. The radiation detector of claim 1, wherein the electronic system comprises an analog-to-digital converter (ADC) configured to digitize the electrical signal.

8. The radiation detector of claim 7, wherein the ADC is a successive-approximation-register (SAR) ADC.

9. The radiation detector of claim 1, wherein the radiation particle is an X-ray photon.

10. The radiation detector of claim 1, further comprising a capacitor module electrically connected to the electric contact, wherein the capacitor module is configured to collect charge carriers from the electric contact.

11. The radiation detector of claim 1, wherein the controller is configured to activate the second voltage comparator at a beginning or expiration of the time delay.

12. The radiation detector of claim 1, wherein the controller is configured to connect the electric contact to an electrical ground.

13. The radiation detector of claim 1, wherein a rate of change of the voltage is substantially zero at expiration of the time delay.

14. The radiation detector of claim 1, wherein the visible light absorption layer comprises a diode.

15. The radiation detector of claim 1, wherein the visible light absorption layer comprises silicon or germanium.

16. A system comprising the radiation detector of claim 1 and a radiation source, wherein the system is configured to perform radiation radiography on human chest or abdomen.

17. A system comprising the radiation detector of claim 1 and a radiation source, wherein the system is configured to perform radiation radiography on human mouth and teeth.

18. A cargo scanning or non-intrusive inspection (NII) system, comprising the radiation detector of claim 1 and a radiation source, wherein the cargo scanning or non-intrusive inspection (NII) system is configured to form an image using backscattered radiation.

19. A cargo scanning or non-intrusive inspection (NII) system, comprising the radiation detector of claim 1 and a radiation source, wherein the cargo scanning or non-intrusive inspection (NII) system is configured to form an image using radiation transmitted through an object inspected.

20. A full-body scanner system comprising the radiation detector of claim 1 and a radiation source.

21. A computed tomography (Radiation CT) system comprising the radiation detector of claim 1 and a radiation source.

22. An electron microscope comprising the radiation detector of claim 1, an electron source and an electronic optical system.

* * * * *